US012617743B2

(12) United States Patent
Franke et al.

(10) Patent No.: US 12,617,743 B2
(45) Date of Patent: May 5, 2026

(54) PROCESS FOR PREPARING THE DIALDEHYDE OF VINYLCYCLOHEXENE

(71) Applicant: EVONIK OPERATIONS GMBH, Essen (DE)

(72) Inventors: Robert Franke, Marl (DE); Carolin Schneider, Monheim am Rhein (DE); Ralf Jackstell, Rostock (DE); Matthias Beller, Ostseebad Nienhagen (DE)

(73) Assignee: EVONIK OXENO GMBH & CO. KG, Marl (DE)

( * ) Notice: Subject to any disclaimer, the term of this patent is extended or adjusted under 35 U.S.C. 154(b) by 398 days.

(21) Appl. No.: 18/345,462

(22) Filed: Jun. 30, 2023

(65) Prior Publication Data

US 2024/0010593 A1 Jan. 11, 2024

(30) Foreign Application Priority Data

Jul. 6, 2022 (EP) .................................... 22183349

(51) Int. Cl.

*C07C 45/50* (2006.01)
*B01J 27/13* (2006.01)
*C07C 29/14* (2006.01)
*C07C 31/27* (2006.01)
*C07C 45/60* (2006.01)
*C07C 47/32* (2006.01)

(52) U.S. Cl.

CPC ............... *C07C 45/60* (2013.01); *B01J 27/13* (2013.01); *C07C 29/14* (2013.01); *C07C 31/276* (2013.01); *C07C 47/32* (2013.01); *C07C 2601/14* (2017.05)

(58) Field of Classification Search

CPC ....... C07C 45/50; C07C 29/14; C07C 31/276; C07C 47/32; B01J 27/13

See application file for complete search history.

(56) References Cited

U.S. PATENT DOCUMENTS

| | | | |
|---|---|---|---|
| 6,252,121 | B1 | 6/2001 | Argyropoulos et al. |
| 2005/0164874 | A1 | 7/2005 | Tsuji |
| 2009/0171125 | A1 | 7/2009 | Shih et al. |
| 2011/0009548 | A1 | 1/2011 | Dakka et al. |
| 2023/0192582 | A1 | 6/2023 | Schneider et al. |
| 2024/0010593 | A1 | 1/2024 | Franke et al. |

FOREIGN PATENT DOCUMENTS

| | | | |
|---|---|---|---|
| AT | 192 395 | B | 10/1957 |
| CN | 1087078 | A | 5/1994 |
| EP | 0 577 042 | A1 | 1/1994 |
| EP | 1065194 | A1 | 1/2001 |
| EP | 4 198 002 | A1 | 6/2023 |
| GB | 1 368 434 | | 9/1974 |
| JP | S53-50102 | A | 5/1978 |
| JP | 2003-505438 | A | 2/2003 |
| JP | 2012-188413 | A | 10/2012 |
| JP | 7585398 | B2 | 11/2024 |
| WO | 01/07382 | A2 | 2/2001 |
| WO | 2011/005822 | A1 | 1/2011 |

OTHER PUBLICATIONS

European Search Report dated Jan. 4, 2023 for European Patent Application No. 22183349.2 (7 pages in German with Machine Translation).

Petöcz, G., et al. Xantphos as cis- and trans-chelating ligand in square-planar platinum(II) complexes. Hydroformylation of styrene with platinum-xantphos-tin(II)chloride system. Journal of Organometallic Chemistry. 2004. vol. 689, pp. 1188-1193.

Garlaschelli, Luigi, et al. Hydroformylation and hydrocarbonylation of dicyclopentadiene with cobalt-rhodium catalytic systems promoted by triphenylphosphine: synthesis of monoformyltryclodecenes, diformyltricyclodecanes and di(tricyclodecenyl)ketones. Journal of Molecular Catalysis. 1991. vol. 68, pp. 7-21.

Van Leeuwen, Piet W.N.M. Xantphos-based, silica-supported, selective, and recyclable hydroformylation catalysts: a review. Journal of Molecular Catalysis A: Chemical. 2002 vol. 182-183, pp. 107-123.

Notice of Reasons for Refusal mailed May 28, 2024 for Japanese Patent Application No. 2023-108019 (4 pages in Japanese; 4 pages English translation).

Arena, Carmela G., et al. Rhodium(I), Palladium(II), and Platinum(II) Complexes Containing New Mixed Phosphane—Phosphite Ligands—Effect of the Catalytic System Stability on the Enantioselective Hydroformylation of Styrene. European Journal of Inorganic Chemistry. 2002. pp. 711-716.

Chinese Office Action mailed May 29, 2025 for Chinese Patent Application No. 202310801297.0 (7 pages in Chinese; 5 pages English translation).

CAS No. 104439-77-2. Tetracarbonyl-μ-hydro[(1,2,3,4,5-η)-1-hydroxylato-2,3,4,5-tetraphenyl-2,4-cyclopentadien-1-yl][(1,2,3,4,5-η)-1-hydroxy-2,3,4,5-tetraphenyl-2,4-cyclopentadien-1-yl]diruthenium. Accessed Jun. 30, 2023. 3 Pages. https://commonchemistry.cas.org/detail?cas_rn=104439-77-2&search=SHVO%27S%20CATALYST.

CAS No. 68478-92-2. Platinum, 1,3-diethenyl-1,1,3,3-tetramethyldisiloxane complexes. Accessed Jun. 30, 2023. 2 Pages. https://commonchemistry.cas.org/detail?cas_rn-68478-92-2&search=68478-92-2.

CAS No. 104439-77-2. SHVO's Catalyst. Accessed Jun. 30, 2023. 2 Pages. https://www.chemicalbook.com/ChemicalProductProperty_EN_CB2246930.htm.

(Continued)

*Primary Examiner* — Sikarl A Witherspoon

(74) *Attorney, Agent, or Firm* — Smith, Gambrell & Russell, LLP

(57) ABSTRACT

Process for preparing the dialdehyde of vinylcyclohexene.

12 Claims, No Drawings

(56) References Cited

OTHER PUBLICATIONS

CAS No. 68478-92-2. Karstedt Catalyst. Platinum(0)-1,3-divinyl-1,1,3,3-tetramethyldisiloxane. Accessed Jun. 30, 2023. 4 Pages. https://www.chemicalbook.com/CASEN_68478-92-2.htm.
Fuchs, Sarah, et al. Synthesis of Industrial Primary Diamines via Intermediate Diols—Combining Hydroformylation, Hydrogenation and Amination. ChemCatChem. 2018. vol. 10, pp. 4126-4133.
Examination Report mailed Dec. 5, 2025 for Indian Patent Application No. 202314043866 (9 pages).

PROCESS FOR PREPARING THE DIALDEHYDE OF VINYLCYCLOHEXENE

The present invention relates to a process for preparing the dialdehyde of vinylcyclohexene.

US 2009/0171125 A1 describes a process for hydroformylation of cyclic olefins. Here, a Rh catalyst is used.

The present invention has the object of providing a novel hydroformylation process. The process here is to afford an increased yield compared to the method known from the prior art.

This object is achieved by a process according to claim 1.

Process comprising the process steps of:

a) initially charging vinylcyclohexene;

b) adding a compound of formula (I):

(I)

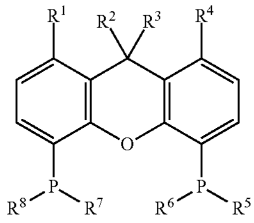

where $R^1$, $R^2$, $R^3$, $R^4$, $R^5$, $R^6$, $R^7$, $R^8$ are selected from: —H, —($C_1$-$C_{12}$)-alkyl, -Ph;

c) adding a Pt compound capable of forming a complex;

d) adding an iodine compound;

e) feeding in CO and $H_2$;

f) heating the reaction mixture from a) to e), to convert the vinylcyclohexene to the dialdehyde.

In this process, process steps a) to e) can be effected in any desired sequence. Typically, however, CO and $H_2$ are added after the co-reactants have been initially charged in steps a) to d).

It is also possible here for process steps c) and d) to be effected in one step, for example by adding $PtI_2$.

In one variant of the process, the Pt compound and the iodine compound are added in one step, by adding $PtI_2$.

The expression ($C_1$-$C_{12}$)-alkyl encompasses straight-chain and branched alkyl groups having 1 to 12 carbon atoms. These are preferably ($C_1$-$C_8$)-alkyl groups, more preferably ($C_1$-$C_6$)-alkyl, most preferably ($C_1$-$C_4$)-alkyl.

Suitable ($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

In one variant of the process, $R^1$ and $R^4$ are —H.

In one variant of the process, $R^5$, $R^6$, $R^7$, $R^8$ are -Ph.

In one variant of the process, $R^2$ and $R^3$ are —($C_1$-$C_{12}$)-alkyl.

In one variant of the process, $R^2$ and $R^3$ are —$CH_3$.

In one variant of the process, the compound (I) has the structure (1):

(1)

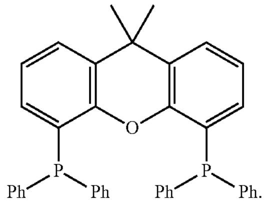

In one variant of the process, the Pt compound is selected from: Pt(II)$I_2$, Pt(IV)$I_4$, diphenyl(1,5-COD)Pt(11), Pt(II)$(acac)_2$, Pt(0)$(PPh_3)_4$, Pt(0)(DVTS) solution (CAS: 68478-92-2), Pt(0)(ethylene)$(PPh_3)_2$, tris(benzylideneacetone)Pt(0), Pt(II)$(OAC)_2$ solution, Pt(0)$(t\text{-}Bu)_2$, Pt(II)(COD)$Me_2$, Pt(II)(COD)$I_2$, Pt(IV)$IMe_3$, Pt(II)(hexafluoroacetylacetonate)$_2$.

In one variant of the process, the Pt compound is selected from: Pt(II)$I_2$, Pt(II)$(acac)_2$.

In one variant of the process, the Pt compound is Pt(II)$I_2$.

In one variant of the process, the iodine compound is selected from: alkali metal halide, alkaline earth metal halide. $NH_4X$, alkylammonium halide, dialkyl halide, trialkyl halide, tetraalkyl halide, cycloalkylammonium halide.

In one variant of the process, the iodine compound is selected from: Pt(II)$I_2$, LiI.

In one variant of the process, $PtI_2$ is added in an amount, measured in mol % based on vinylcyclohexene, so that the value is in the range of 0.1 mol % to 5 mol %.

In one variant of the process, $PtI_2$ is added in an amount, measured in mol % based on vinylcyclohexene, so that the value is in the range of 0.1 mol % to 3 mol %.

In one variant of the process, $PtI_2$ is added in an amount, measured in mol % based on vinylcyclohexene, so that the value is in the range of 0.1 mol % to 1 mol %.

In one variant of the process, this process comprises the additional process step e'): e') adding a solvent.

In one variant of the process, the solvent is selected from: THF, DCM, ACN, heptane, DMF, toluene, texanol, pentane, hexane, octane, isooctane, decane, dodecane, cyclohexane, benzene, xylene, Marlotherm, propylene carbonate, MTBE, diglyme, triglyme, diethyl ether, dioxane, isopropanol, tert-butanol, isononanol, isobutanol, isopentanol, ethyl acetate.

In one variant of the process, the solvent is selected from: THF, DCM, ACN, heptane, DMF, toluene, texanol.

In one variant of the process, CO and $H_2$ are fed in at a pressure in a range from 1 MPa (10 bar) to 6 MPa (60 bar).

In one variant of the process, CO and $H_2$ are fed in at a pressure in a range from 1 MPa (20 bar) to 6 MPa (50 bar).

In one variant of the process, the reaction mixture is heated to a temperature in the range from 30° C. to 150° C.

In one variant of the process, the reaction mixture is heated to a temperature in the range from 80° C. to 140° C.

In one variant of the process, the process comprises the additional process step g): g) converting the dialdehyde to the diol.

In one variant of the process, the conversion of the dialdehyde to the diol is carried out using "Shvo's catalyst" (CAS 104439-77-2).

In addition to the process, also claimed are the aldehyde mixture (2a) and (2b), and the alcohol mixture (3a) and (3b).

Aldehyde mixture comprising the compounds (2a) and (2b):

(2a)

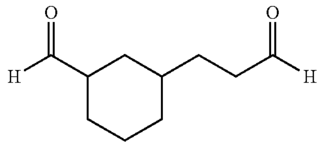

(2b)

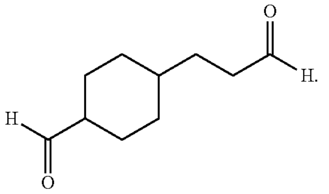

Alcohol mixture comprising the compounds (3a) and (3b):

(3a)

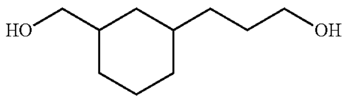

(3b)

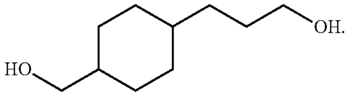

The invention shall be elucidated in more detail hereinbelow with reference to a working example.

EXPERIMENTAL DESCRIPTION

Conversion of Vinylcyclohexene to the Dialdehyde

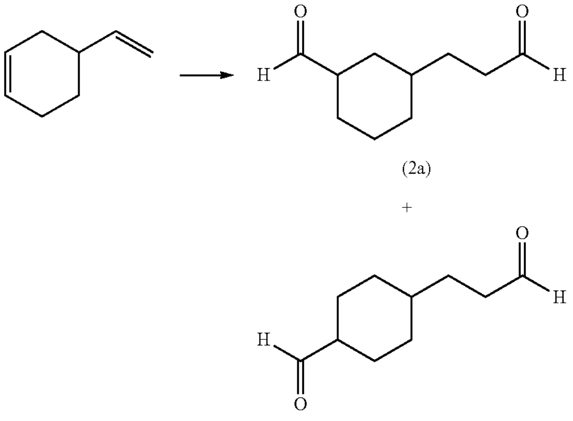

(2a)

+

(2b)

10 mmol of 4-vinylcyclohex-1-ene, 10 ml of absolute toluene, 0.5 mol % $PtI_2$, 2.2 equivalents of xantphos (1) (based on Pt) are placed under argon in a 25 ml steel autoclave from Parr Instruments. The autoclave is pressurized to 40 bar with synthesis gas ($CO/H_2$=1:1) and the reaction started by heating to 120° C. and stirring. This reaction is conducted at 40 bar/120° C. for 3.5 h. The autoclave is then cooled, the pressure released and a GC sample taken.

In a comparative experiment, $Rh(acac)(CO)_2$ was added instead of $PtI_2$.

The reaction with $Rh(acac)(CO)_2$ ran over 11 h.

Yield of dialdehyde (2a)+(2b):

$PtI_2$: 92%

$Rh(acac)(CO)_2$: <14%

Conversion of the Dialdehyde to the Diol.

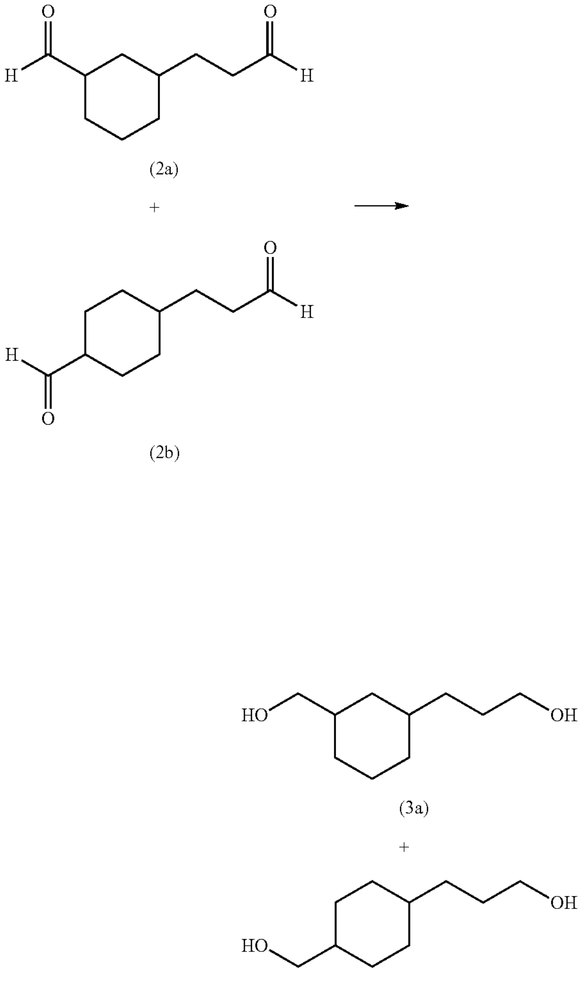

(2a)

+

(2b)

(3a)

+

(3b)

30 mmol of the isomeric mixture of the dialdehyde, 25 ml of absolute toluene, 176 mg of "Shvo's catalyst" (CAS 104439-77-2) are transferred under argon to a 100 ml Parr pressure autoclave. The autoclave is pressurized to 50 bar with hydrogen and the reaction carried out with stirring at 100° C. for 1 h and at 110° C. for a further 30 minutes. The reaction is then discontinued (autoclave cooled and the pressure released). The reaction solution is transferred to a Schlenk vessel. Two phases are formed, the lower phase is isolated and freed of toluene in vacuo. This gives the isomeric mixture of the diol (3a)+(3b).

Yield of diol (3a)+(3b): 85%

As the experimental results show, the object is achieved by the process according to the invention.

The invention claimed is:

1. Process comprising the process steps of:

a) initially charging vinylcyclohexene;

b) adding a compound of formula (I):

(I)

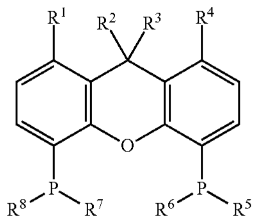

where $R^1$, $R^2$, $R^3$, $R^4$, $R^5$, $R^6$, $R^7$, $R^8$ are selected from: —H, —$(C_1\text{-}C_{12})$-alkyl, -Ph;

c) adding a Pt compound capable of forming a complex;

d) adding an iodine compound;

e) feeding in CO and $H_2$;

f) heating the reaction mixture from steps a) to e), to convert the vinylcyclohexene to the dialdehyde and g) converting the dialdehyde to the diol.

2. Process according to claim 1, where $R^1$ and $R^4$ are —H.

3. Process according to claim 1, where $R^5$, $R^6$, $R^7$, $R^8$ are -Ph.

4. Process according to claim 1, where $R^2$ and $R^3$ are —$(C_1\text{-}C_{12})$-alkyl.

5. Process according to claim 1, where $R^2$ and $R^3$ are —$CH_3$.

6. Process according to claim 1, wherein the compound (I) has the structure (1):

(1)

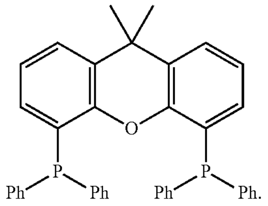

7. Process according to claim 1, wherein the Pt compound is selected from: $Pt(II)I_2$, $Pt(IV)I_4$, diphenyl(1,5-COD)Pt(II), $Pt(II)(acac)_2$, $Pt(0)(PPh_3)_4$, Pt(0)(DVTS) solution (CAS: 68478-92-2), $Pt(0)(ethylene)(PPh_3)_2$, tris(benzylideneacetone)Pt(0), $Pt(II)(OAC)_2$ solution, $Pt(0)(t\text{-}Bu)_2$, $Pt(II)(COD)Me_2$, $Pt(II)(COD)I_2$, $Pt(IV)IMe_3$, Pt(II)(hexafluoroacetylacetonate)$_2$.

8. Process according to claim 1, wherein $PtI_2$ is added in an amount, measured in mol % based on vinylcyclohexene, so that the value is in the range of 0.1 mol % to 5 mol %.

9. Process according to claim 1, comprising the additional process step e'):

e') adding a solvent.

10. Process according to claim 1, wherein the conversion of the dialdehyde to the diol is carried out using "Shvo's catalyst" (CAS 104439-77-2).

11. Aldehyde mixture comprising the compounds (2a) and (2b):

(2a)

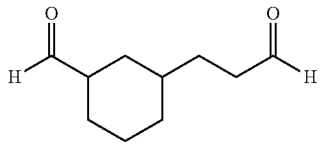

(2b)

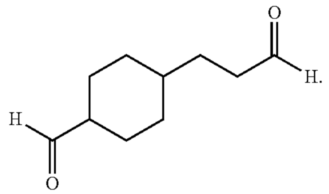

12. Alcohol mixture comprising the compounds (3a) and (3b):

(3a)

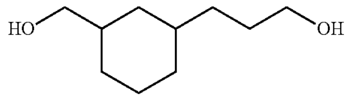

(3b)

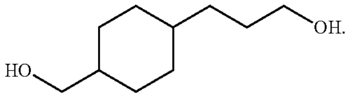

* * * * *